United States Patent [19]

Chabardes

[11] Patent Number: 4,749,814
[45] Date of Patent: Jun. 7, 1988

[54] PROCESS FOR THE PREPARATION OF ETHYLENIC CARBONYL COMPOUNDS

[75] Inventor: Pierre Chabardes, Sainte Foy les Lyon, France

[73] Assignee: Rhone-Poulenc Sante, Courbevoie, France

[21] Appl. No.: 33,460

[22] Filed: Apr. 2, 1987

[30] Foreign Application Priority Data

Apr. 3, 1986 [FR] France ................... 86 04769

[51] Int. Cl.$^4$ ................................. C07C 45/51
[52] U.S. Cl. ....................... 568/384; 568/310; 568/341; 568/427; 568/450; 568/443
[58] Field of Search .......... 568/310, 341, 384, 427, 568/443, 450

[56] References Cited

U.S. PATENT DOCUMENTS

| | | | |
|---|---|---|---|
| 3,919,250 | 11/1975 | Pauling | 568/450 |
| 3,920,751 | 11/1975 | Chebardes et al. | 568/450 |
| 3,994,936 | 11/1976 | Andrews et al. | 568/450 |
| 4,495,371 | 1/1985 | Neri et al. | 568/427 |

FOREIGN PATENT DOCUMENTS

| | | | |
|---|---|---|---|
| 0127536 | 12/1984 | European Pat. Off. | 568/384 |
| 1554805 | 1/1969 | France | 568/384 |
| 1576228 | 6/1969 | France | 568/384 |
| 96549 | 11/1972 | France | 568/341 |
| 57-116024 | 7/1982 | Japan | 568/450 |
| 1228663 | 4/1971 | United Kingdom | 568/384 |

*Primary Examiner*—James H. Reamer
*Attorney, Agent, or Firm*—Stevens, Davis, Miller & Mosher

[57] ABSTRACT

Ethylenic carbonyl compounds of formula

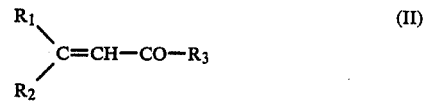

(II)

are made by the isomerization of acetylenic alcohols of formula

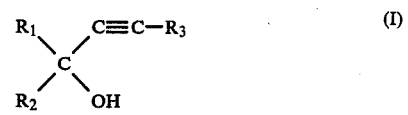

(I)

in the presence of a catalyst consisting of a titanium derivative, a copper or silver derivative, and, if required, an acid, which may be in the form of an ester or anhydride, or an inorganic ester.

11 Claims, No Drawings

PROCESS FOR THE PREPARATION OF ETHYLENIC CARBONYL COMPOUNDS

The present invention relates to the preparation of ethylenic carbonyl compounds by the isomerization of α-acetylenic alcohols.

The isomerization in an acid medium of arylalkynylcarbinols into ethylenic carbonyl compounds is known [K. H. MEYER et al., Ber. 55, 819–823 (1922); M. BADOCHE, Bull. Soc. Chim. (France), (4), 43, 340 (1928); W. S. MacGREGOR, J. Amer. Chem. Soc., 70, 3953 (1948); N. HAGIHARA, Chem. Abstr. 45, 8997 g (1951); E. T. CLAPPERTON et al., J. Amer. Chem. Soc., 72, 2501-2 (1950)]. Subjecting secondary or tertiary acetylenic alcohols in the vapour phase to the action of acid catalysts with a view to obtaining mixtures of unsaturated aldehydes, unsaturated ketones and acetylenic ethylenic hydrocarbons is also known [U.S. Pat. No. 2,524,865; E. D. BERGMANN, J. Amer. Chem. Soc., 73, 1218–1220 (1951)]. The isomerization of methylbutynol into prenal in the presence of a catalyst based on molybdenum oxide deposited on silica, operating at 350°–400° C., in order to obtain a good selectivity is also known (Russian Patent SU No. 827,477).

However, these processes can be used on an industrial scale only with difficulty.

The catalytic isomerization of acetylenic alcohols into ethylenic carbonyl compounds by heating in a liquid phase in the presence of a catalyst based on a metal chosen from the group consisting of vanadium, niobium, molybdenum, tungsten and rhenium, and more particularly a metal derivative which comprises a linkage having one of the following formulae:

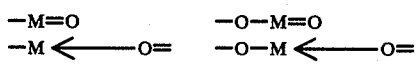

M representing a metal atom such as, e.g. cyclohexyl orthovanadate, is also known from French Patent FR No. 1,554,805 and its addition FR No. 95,548.

However, it is not possible to achieve a complete conversion of α-acetylenic alcohol unless the reaction is carried out in a very dilute medium and in the presence of silanols, which are expensive.

It has now been found, and this forms the subject of the present invention, that acetylenic alcohols of formula:

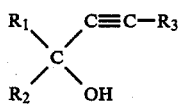

can be isomerized directly into carbonyl compounds of formula:

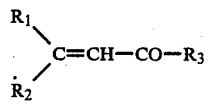

by heating in a liquid phase in the presence of a catalytic system which comprises a titanium derivative and a copper of silver derivative and, optionally, an inorganic or organic acid ester, and acid anhydride, or preferably, an organic acid and then isolating the ethylenic carbonyl compound obtained.

In general formulae (I) and (II), $R_1$, $R_2$ and $R_3$, which may be identical or different, each represent a hydrogen atom or a saturated or unsaturated aliphatic radical, a saturated or unsaturated alicyclic radical, an aromatic radical, or an arylaliphatic radical, or $R_1$ and $R_2$ together form a divalent radical and $R_3$ represents a hydrogen atom or a saturated or unsaturated aliphatic radical, a saturated or unsaturated alicyclic radical, an aromatic radical or an arylaliphatic radical, the aforesaid aliphatic, alicyclic, aromatic and arylaliphatic radicals being unsubstituted or substituted by one or more substituents, which may be identical or different, chosen from halogen, hydroxy, alkoxy, phenoxy, acyl and acyloxy.

Preferably, $R_1$, $R_2$ and $R_3$ together contain 2 to 30 carbon atoms and at least one of the radicals $R_1$ and $R_2$ is a hydrogen atom or an unsubstituted or substituted saturated or unsaturated alkyl radical containing 1 to 15 carbon atoms.

Products of general formula (II) in which $R_3$ represents a hydrogen atom are of a very particular value.

The process according to the invention is particularly useful for the isomerization of methylbutynol into prenal (i.e. of 3-methyl-butyn-3-ol into 3-methyl-but-2-enal) or of dehydrolinalol into citral; prenal and citral are particularly valuable intermediates for the preparation of vitamin A or of vitamin E.

For implementing the process of the invention, it is essential to use a catalytic system which simultaneously contains the titanium derivative and the copper or silver derivative and, if required, an organic acid or a derivative (ester or anhydride) thereof or an inorganic ester.

In the titanium derivative the titanium may have a degree of oxidation of II, III or IV. Titanium derivatives which are particularly well suited are derivatives of general formula $TiR_4$ is which the symbols R, which may be identical or different, each represent a halogen atom or an OR' or OCOR' radical (in which R' represents an alkyl radical containing 1 to 20 carbon atoms), an $—OSiR_1R_2R_3$ radical (in which the symbols $R_1$, $R_2$ and $R_3$, which may be identical or different, represent an alkyl radical such as methyl or ethyl or an aryl radical such as phenyl). Chelates of titanium such as chelates of titanium with acetylacetone, benzoylacetone, alkyl acetylacetates or salicylaldehyde may also be advantageously used. Titanium derivatives used in the process of the invention may be, e.g., alkyl titanates of formula $Ti(OR_5)_4$ such as butyl or isopropyl titanate, carboxylic acid salts of formula $Ti(OCOR_6)_4$ or mixed derivatives of formula $Ti(OR_5)_{4-n}(OCOR_6)_n$ or $Ti(OR_5)_n(OSiR_1R_2R_3)_{4-n}$ or $Ti(OR_5)_2$(chelating agent)$_2$ or $TiCl_2(OCOR_6)_2$ and polytitanates. These titanium derivatives are described especially in "The Organic Chemistry of Titanium" by FELD and COWE, London, Butterworths (1965).

Among derivatives of titanium with different degrees of oxidation, which may be used for implementing the process according to the invention, there may be mentioned, e.g. titanium trichloride, titanium oxyhalides such as $TiOCl_2$, $TiOCl$, $TiOBr$, oxytitanium compounds such as titanyl sulphate, titanocene dichloride, titanyl acetylacetonate, $TiO(SbF_6)_2$, $TiO(TiF_6)$, $TiO[(C_2H_5)_4N]_2Cl_4$, TiO(phthalocyanine), titanium derivatives of formula $O=T(X)_2$, in which X represents an OR' or OCOR' radical defined as above, and, more generally, titanium derivatives which are described by M. Bottrill et al., Comprehensive Organic Chemistry, Vol. 8, p. 332–426 (1982) edited by Wilkinson, Pergamon Press or by R. J. H. Clark, The Chemistry of Titanium, Zirconium and Hafnium, Pergamon Texts in Inorganic Chemistry, Vol. 19, (1973), Pergamon Press.

The titanium derivatives may be prepared, if required, in situ by introducing into the reaction mixture the reagents required for their formation.

Among the titanium derivatives which are particularly well suited, butyl titanate or isopropyl titanate may be mentioned.

The copper or silver derivatives are chosen from amongst inorganic or organic acid salts or metal complexes. Particularly satisfactory results are obtained using cuprous chloride, cupric chloride or cupric oxalate or silver trifluoroacetate.

The organic acids, which may be used, if required, in the ester or anhydride form, are chosen from amongst saturated or unsaturated aliphatic acids or diacids containing 1 to 20 carbon atoms (such as acetic, hexanoic, heptanoic, 2-ethylhexanoic, octanoic, adipic or crotonic acids) and aromatic acids or diacids (such as benzoic or terephthalic acids), which may be substituted if required (such as 4-methylbenzoic, 4-methoxybenzoic or 4-phenoxybenzoic acids) or arylaliphatic acids (phenylacetic acid). It is also possible to use an enol ester such as 2-acetoxypropene. The inorganic esters are chosen from amongst phosphoric acid esters (such as tributylphosphate) or sulphonic acid esters (such as butyl para-toluenesulphonate).

It is particularly advantageous to implement the process according to the present invention in the presence of an organic acid.

In general, for one mole of acetylenic alcohol of general formula (I) employed, 0.005 to 0.05 mole of titanium derivative, 0.005 to 0.1 mole of copper derivative and 0.01 to 1 mole of organic acid or its derivative or of inorganic ester are used.

In general, the process according to the invention is operated at a temperature of 80° to 180° C., preferably in the vicinity of 130° C., the reaction being complete after 1 to 2 hours of heating. It is possible to operate in an organic solvent chosen from amongst aliphatic, alicyclic or aromatic hydrocarbons, which may be substituted, if required, with one or more halogen atoms or alkoxy, nitro or cyano radicals, such as dichloroethane, dichlorobenzene, anisole, phenetole, nitrobenzene, bicyclohexyl or benzonitrile, amides (N-methylpyrrolidone) or ketones (cyclohexanone). Organic acids, which may be, if required, in the ester or anhydride form, may also be used as solvents.

When an organic ester (butyl acetate) is used, it may be advantageous to operate in the presence of an alcohol (butanol) or a silanol (triphenylsilanol) but, in this case, it is essential that the molar ratio of silanol to the titanium derivative is less than 4.

The process according to the present invention may be carried out continuously or in batches. The catalyst may be recovered at the end of the reaction and reused in new isomerization operations.

The ethylenic carbonyl compound of general formula (II) obtained by the process of the present invention may be isolated by any means known per se, e.g. by distillation or by means of a sulphite or bisulphite combination in the case of aldehydes. For some applications, there is no need to isolate the ethylenic carbonyl compound and all of the products which form the reaction medium may be used directly for carrying out syntheses from the ethylenic carbonyl compound obtained. This is so, e.g., in the case of the preparation of ionones from citral, which is obtained by the isomerization of dehydrolinalol.

The following examples illustrate the invention.

EXAMPLE 1

(1) The following are introduced, under an argon atmosphere, into a 50-cc three-necked round-bottomed flask equipped with a condenser, an inlet for argon and a partition-wall for sampling and a magnetic stirrer:

| | |
|---|---|
| methylbutynol | 12.8 g (152.2 mmoles) |
| 4-methylbenzoic acid | 3.6 g (26.4 mmoles) |
| dichlorobenzene | 19.6 g |
| bicyclohexyl (internal standard for chromatography) | 5.3 g |
| butyl titanate | 0.75 g (2.20 mmoles) |
| cuprous chloride | 0.3 g (3.03 mmoles) |

The flask is heated with an oil bath, the temperature of which is adjusted to 130° C. In 12 minutes, the temperature of the reaction mixture passes from 50° to 126° C. and a yellow precipitate is formed. After 15 minutes, the temperature rises to 137° C. and then stabilizes at 125°–126° C. After stirring at this temperature for 1 hour, the reaction mixture is cooled to a temperature in the vicinity of 20° C.

Analysis of the crude reaction product by gas chromatography shows that: the degree of conversion of methylbutynol is 96.6% and the yield of prenal relative to the methylbutynol converted is 90%.

The crude reaction product, which is heterogeneous, is distilled under reduced pressure (15 mm Hg; 2 kPa), heating to a maximum temperature of 72° C. The following are thereby obtained:

a colourless distillate (13.2 g), analysis of which shows that the degree of conversion of methylbutynol is 96.3% and that the yield of prenal is 86% relative to the methylbutynol converted; and a residue (28.8 g), analysis of which shows that it contains 1% of prenal.

(2) Methylbutynol (12.8 g) is added to the residue obtained as described above (28.8 g) and the mixture is heated for 1 hour 30 minutes with an oil bath, the temperature of which is adjusted to 130° C.

Analysis of the crude reaction product by gas chromatography shows that: the degree of conversion of methylbutynol is 94% and the yield of prenal relative to the methylbutynol converted is 90%.

The crude reaction product is distilled under reduced pressure (15 mm Hg; 2 kPa), heating to a maximum temperature of 73° C. The following are thereby obtained:

a colourless distillate (13.9 g), analysis of which shows that the degree of conversion of methylbutynol is 94% and that the yield of prenal is 89% relative to the methylbutynol converted; and a residue (27.35 g), analysis of which shows that it contains 1.1% or prenal.

(3) Methylbutynol (12.8 g) and dichlorobenzene (2.9 g) are added to the residue obtained as described above (27.35 g) and the mixture is heated for 2 hours with an oil bath, the temperature of which is adjusted to 130° C.

Analysis of the crude reaction product by gas chromatography shows that the degree of conversion of methylbutynol is 88% and the yield of prenal is 91% relative to the methylbutynol converted.

The crude reaction is distilled under reduced pressure (20 mm Hg; 2.7 kPa), heating to a maximum temperature of 72° C.

A colourless distillate (12.4 g) is thereby obtained, analysis of which shows that the degree of conversion of methylbutynol is 87% and that the yield of prenal is 82% relative to the methylbutynol converted.

Analysis of the three colourless distillates combined together shows that the mean degree of conversion is 92% and that the mean yield of prenal is 85.4% relative to the methylbutynol converted. The mean yield of prenal, for the three operations, is 78.6% relative to the methylbutynol employed.

EXAMPLE 2

The following are introduced, under an inert atmosphere, into a 25-cc three-necked round-bottomed flask equipped with a condenser, an inlet for argon, a partition-wall for sampling and a magnetic stirrer:

| methylbutynol | 4.34 g (51.6 mmoles) |
| ethyl acetate | 4.5 g (51.1 mmoles) |
| butyl titanate | 0.5 g (1.46 mmoles) |

The contents are heated for 4 hours at a temperature of between 80° and 90° C. Analysis by gas chromatography shows that no prenal is formed. Cuprous chloride (0.5 g; 5.05 mmoles) is then added. After heating at 90° C. for 2 hours, testing by gas chromatography (surface measurement) shows that the degreee of conversion of methylbutynol is approximately 80% and that the yield of prenal is 65% relative to the methylbutynol converted.

EXAMPLE 3

The reaction is carried out as in Example 2, but in the absence of butyl titanate.

After heating at 90° C. for 1 hour 30 minutes, the methylbutynol is recovered unchanged.

EXAMPLE 4

The reaction is carried out as in Example 2, but using:

| methylbutynol | 4.34 g (51.6 mmoles) |
| methyl benzoate | 5.43 g (39.8 mmoles) |
| butyl titanate | 0.25 g (0.73 mmoles) |

After heating at 130° C. for 3 hours, no formation of prenal is observed.

Cuprous chloride (0.1 g; 1.01 mmole) is then added and the mixture is heated for 2 hours at 130° C.

Testing by gas chromatography (surface measurement) shows that the degree of conversion of methylbutynol is close to 100% and that the yield of prenal is 58%.

EXAMPLE 5

The reaction is carried out as in Example 4, but using:

| methylbutynol | 4.34 g (51.6 mmoles) |
| tributyl phosphate | 4.9 g (18.4 mmoles) |
| butyl titanate | 0.25 g (0.73 mmole) |
| cuprous chloride | 0.1 g (1.01 mmole) |

After heating at 130° C. for 2 hours, chromatographic analysis shows that the degree of conversion of methylbutynol is close to 100% and that the yield of prenal is close to 60%.

EXAMPLE 6

The reaction is carried out as in Example 5, but in the absence of a cuprous chloride. After heating at 140° C. for 2 hours, no formation of prenal is observed.

EXAMPLE 7

The reaction is carried out as in Example 2 but using:

| methylbutynol | 4.34 g (51.6 mmoles) |
| methyl benzoate | 0.5 g (3.68 mmoles) |
| bicyclohexyl (internal standard) | 1.75 g |
| dichlorobenzene | 26 g |
| butyl titanate | 0.25 g (0.75 mmole) |
| cuprous chloride | 0.1 g (1.01 mmole) |

The mixture is heated for 2 hours at 120° C.

The degree of conversion of methylbutynol is 98.5% and the yield of prenal is 62% relative to the methylbutynol converted.

EXAMPLE 8

The reaction is carried out as in Example 2, but using:

| methylbutynol | 4.34 g (51.6 mmoles) |
| 2-acetoxypropene | 0.3 g (3.05 mmoles) |
| bicyclohexyl (internal standard) | 1.76 g |
| butyl titanate | 0.25 g (0.73 mmole) |
| cuprous chloride | 0.1 g (1.01 mmole) |

The mixture is heated at 110° C. for 4 hours 30 minutes.

The degree of conversion of methylbutynol is 98.5% and the yield of prenal is 55% relative to the methylbutylnol converted.

EXAMPLE 9

The reaction is carried out as in Example 2, but using:

| methylbutynol | 4.34 g (51.6 mmoles) |
| butyl acetate | 4.38 g (37.7 mmoles) |
| butanol | 0.41 g (5.5 mmoles) |
| bicyclohexyl (internal standard) | 1.74 g |
| butyl titanate | 0.25 g (0.73 mmole) |
| cuprous chloride | 0.1 g (1.01 mmole) |

The mixture is heated at 120° C. for 2 hours 30 minutes.

The degree of conversion of methylbutynol is 98.5% and the yield of prenal is 61% relative to the methylbutynol converted.

EXAMPLE 10

The reaction is carried out as in Example 2, but using:

| methylbutynol | 4.36 g (51.9 mmoles) |

-continued

| | |
|---|---|
| methyl benzoate | 5.44 g (40 mmoles) |
| triphenylsilanol | 0.43 g (1.55 mmoles) |
| bicyclohexyl (internal standard) | 1.76 g |
| butyl titanate | 0.29 g (0.86 mmoles) |
| cuprous chloride | 0.11 g (1.1 mmole) |

The mixture is heated at 130° C. for 2 hours 30 minutes.

The degree of conversion of methylbutynol is 96% and the yield of prenal is 60% relative to the methylbutylnol converted.

EXAMPLE 11

The reaction is carried out as in Example 2, but using:

| | |
|---|---|
| methylbutynol | 4.35 g (51.8 mmoles) |
| methylbutynol acetate | 0.51 g (4.04 mmoles) |
| bicyclohexyl (internal standard) | 1.75 g |
| dichlorobenzene | 13.10 g |
| butyl titanate | 0.25 g (0.75 mmole) |
| cuprous chloride | 0.101 g (1.02 mmole) |

The mixture is heated at 130° C. for 1 hour 30 minutes.

The degree of conversion of methyl butynol is 97% and the yield of prenal is 61% relative to the methylbutynol converted.

EXAMPLE 12

The reaction is carried out as in Example 2, but using:

| | |
|---|---|
| methylbutynol | 4.34 g (51.6 mmoles) |
| methyl benzoate | 5.42 g (39.8 mmoles) |
| acetic acid | 0.525 g (8.74 mmoles) |
| bicyclohexyl (internal standard) | 1.73 g |
| butyl titanate | 0.25 g (0.73 mmole) |
| cuprous chloride | 0.1 g (1.01 mmole) |

The mixture is heated at 130° C. for 2 hours.

The degree of conversion of methylbutynol is 99% and the yield of prenal is 67% relative to the methylbutynol converted.

EXAMPLE 13

The reaction is carried out as in Example 2, but using:

| | |
|---|---|
| methylbutynol | 4.34 g (51.6 mmoles) |
| acetic acid | 0.525 g (8.74 mmoles) |
| bicyclohexyl (internal standard) | 1.728 g |
| dichlorobenzene | 6.55 g |
| butyl titanate | 0.25 g (0.73 mmole) |

After heating at 130° C. for 2 hours, no formation of prenal is observed.

Cuprous chloride (0.1 g; 1.01 mmole) is then added and the mixture is heated at 130° C. for 1 hour 30 minutes.

The degree of conversion of methylbutynol is 92% and the yield of prenal is 78% relative to the methylbutynol converted.

EXAMPLE 14

The reaction is carried out as in Example 13, but in the absence of butyl titanate.

After heating at 130° C. for 2 hours, no formation of prenal is observed.

EXAMPLE 15

The reaction is carried out as in Example 2, but using:

| | |
|---|---|
| methylbutynol | 4.34 g (51.6 mmoles) |
| acetic anhydride | 0.324 g (3.17 mmoles) |
| dichlorobenzene | 6.55 g |
| bicyclohexyl (internal standard) | 1.73 g |
| butyl titanate | 0.25 g (0.73 mmole) |
| cuprous chloride | 0.1 g (1.01 mmole) |

After heating at 130° C. for 30 minutes, the degree of conversion of methylbutynol is 88% and the yield of prenal is 80% relative to the methylbutynol converted.

After heating at 130° C. for 1 hour 30 minutes, the degree of conversion of methylbutynol is close to 100% and the yield of prenal is 66% relative to the methylbutynol converted.

EXAMPLE 16

The reaction is carried out as in Example 2, but using:

| | |
|---|---|
| methylbutynol | 4.34 g (51.6 mmoles) |
| benzoic acid | 1 g (8.19 mmoles) |
| bicyclohexyl (internal standard) | 1.73 g |
| dichlorobenzene | 6.55 g |
| butyl titanate | 0.25 g (0.73 mmole) |
| cuprous chloride | 0.1 g (1.01 mmole) |

After heating at 130° C. for 1 hour 30 minutes, the degree of conversion of methylbutynol is 95% and the yield of prenal is 79% relative to the methylbutynol converted.

EXAMPLE 17

The reaction is carried out as in Example 2, but using:

| | |
|---|---|
| methylbutynol | 4.34 g (51.6 mmoles) |
| terephthalic acid | 0.8 g (4.81 mmoles) |
| bicyclohexyl (internal standard) | 1.73 g |
| dichlorobenzene | 6.55 g |
| butyl titanate | 0.25 g (0.73 mmole) |
| cuprous chloride | 0.1 g (1.01 mmole) |

After heating at 130° C. for 1 hour, the degree of conversion of methylbutynol is 98% and the yield of prenal is 76% relative to the methylbutynol converted.

EXAMPLE 18

The reaction is carried out as in Example 2, but using:

| | |
|---|---|
| methylbutynol | 4.34 g (51.6 mmoles) |
| 4-methylbenzoic acid | 1.2 g (8.81 mmoles) |
| bicyclohexyl (internal standard) | 1.73 g |

| | |
|---|---|
| dichlorobenzene | 6.55 g |
| butyl titanate | 0.25 g (0.73 mmole) |
| cuprous chloride | 0.1 g (1.01 mmole) |

The mixture is heated to 130° C. and the progress of the reaction mixture is monitored by gas chromatography:

after 30 minutes, the degree of conversion of methylbutynol is 94% and the yield of prenal is 91% relative to the methylbutynol converted, after 1 hour, the degree of conversion of methylbutynol is 97% and the yield of prenal is 89% relative to the methylbutynol converted and after 1 hour 30 minutes, the degree of conversion of methylbutynol is 98% and the yield of prenal is 86% relative to the methylbutynol converted.

EXAMPLE 19

The reaction is carried out as in Example 2, but using:

| | |
|---|---|
| methylbutynol | 4.34 g (51.6 mmoles) |
| hexanoic acid | 1.02 g (8.78 mmoles) |
| bicyclohexyl (internal standard) | 1.73 g |
| dichlorobenzene | 6.55 g |
| butyl titanate | 0.25 g (0.73 mmole) |
| cuprous chloride | 0.1 g (1.01 mmole) |

The mixture is heated to 130° C. and the progress of the reaction mixture is monitored by gas chromatography:

after 30 minutes, the degree of conversion of methylbutynol is 87% and the yield of prenal is 91% relative to the methylbutynol converted, after 1 hour, the degree of conversion of methylbutynol in 95% and the yield of prenal is 86% relative to the methylbutynol converted and after 1 hour 30 minutes, the degree of conversion of methylbutynol is 97% and the yield of prenal is 84% relative to the methylbutynol converted.

EXAMPLE 20

The reaction is carried out as in Example 2, but using:

| | |
|---|---|
| methylbutynol | 4.34 g (51.6 mmoles) |
| adipic acid | 0.65 g (4.45 mmoles) |
| bicyclohexyl (internal standard) | 1.73 g |
| dichlorobenzene | 6.55 g |
| butyl titanate | 0.25 g (0.73 mmole) |
| cuprous chloride | 0.1 g (1.01 mmole) |

After heating at 130° C. for 4 hours, the degree of conversion of methylbutynol is 82% and the yield of prenal is 74% relative to the methylbutynol converted.

EXAMPLE 21

The reaction is carried out as in Example 2, but using:

| | |
|---|---|
| dehydrolinalol | 4 g (26.3 mmoles) |
| butyl acetate | 4.375 g (37.7 mmoles) |
| bicyclohexyl (internal standard) | 1.72 g |
| butyl titanate | 0.13 g (0.38 mmole) |
| cuprous chloride | 0.1 g (1.01 mmole) |

After heating at 130° C. for 3 hours, the degree of conversion of dehydrolinalol is 93% and the yield of citral is 45% relative to the dehydrolinalol converted.

EXAMPLE 22

The reaction is carried out as in Example 2, but using:

| | |
|---|---|
| methylbutynol | 4.34 g (51.6 mmoles) |
| dichlorobenzene | 6.55 g |
| bicyclohexyl (internal standard) | 1.73 g |
| butyl titanate | 0.25 g (0.73 mmole) |
| cuprous chloride | 0.10 g (1.01 mmole) |

After heating at 130° C. for 1 hour 30 minutes, the degree of conversion of methylbutynol is 99% and the yield of prenal is 60% relative to the methylbutynol converted.

EXAMPLE 23

The reaction is carried out as in Example 2, but using:

| | |
|---|---|
| methylbutynol | 4.34 g (51.6 mmoles) |
| 4-methylbenzoic acid | 1.2 g (8.81 mmoles) |
| bicyclohexyl (internal standard) | 3.46 g |
| dichlorobenzene | 13.1 g |
| titanium dibutoxy-bis-acetylacetonate | 0.3 g (0.72 mmole) |
| cuprous chloride | 0.10 g (1.01 mmole) |

After heating at 130° C. for 2 hours, the degree of conversion of methylbutynol is 98% and the yield of prenal is 88% relative to the methylbutynol converted.

EXAMPLE 24

The reaction is carried out as in Example 2, but using:

| | |
|---|---|
| methylbutynol | 4.34 g (51.6 mmoles) |
| 4-methylbenzoic acid | 1.2 g (8.81 mmoles) |
| bicyclohexyl (internal standard) | 1.73 g |
| dichlorobenzene | 6.55 g |
| butyl titanate | 0.25 g (0.73 mmole) |
| cuprous chloride | 0.15 g (1.12 mmole) |

After heating at 130° C. for 1 hour 30 minutes, the degrees of conversion of methylbutynol is 97% and the yield of prenal is 77% relative to the methylbutynol converted.

EXAMPLE 25

The reaction is carried out as in Example 2, but using:

| | |
|---|---|
| methylbutynol | 4.34 g (51.6 mmoles) |
| 4-methylbenzoic acid | 1.2 g (8.81 mmoles) |
| bicyclohexyl (internal standard) | 1.73 g |
| dichlorobenzene | 6.55 g |
| butyl titanate | 0.25 g (0.73 mmole) |

| silver trifluoroacetate | 0.22 g (1.0 mmole) |

After heating at 130° C. for 2 hours, the degree of conversion of methylbutynol is 61% and the yield of prenal is 82% relative to the methylbutynol converted.

EXAMPLE 26

The reaction is carried out as in Example 2, but using:

| 2,2,6-trimethyl-1-ethy-nyl-1-cyclohexanol | 9.2 g (55.3 mmoles) |
| 4-methylbenzoic acid | 1.2 g (8.81 mmoles) |
| dichlorobenzene | 13.1 g |
| bicyclohexyl (internal standard) | 3.5 g |
| butyl titanate | 0.25 g (0.73 mmole) |
| cuprous chloride | 0.10 g (1.01 mmole) |

After heating at 130° C. for 4 hours, the degree of conversion of 2,2,6-trimethyl-1-ethynyl-1-cyclohexanol is 96%.

A mixture of (2,2,6-trimethylcyclohexylidene)formaldehyde(A) and (2,6,6-trimethyl-1-cyclohexenyl)acetaldehyde(B) in a molar ratio of 0.34 is obtained, in quantitative yield.

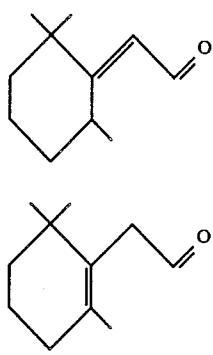

The (2,2,6-trimethylcyclohexylidene)formaldehyde may be isomerized into (2,6,6-trimethyl-1-cyclohexenyl)acetaldehyde.

EXAMPLE 27

The reaction is carried out as in Example 2, but using:

| dehydrolinalol | 4 g (26.3 mmoles) |
| 4-methylbenzoic acid | 0.6 g (4.41 mmoles) |
| dichlorobenzene | 6.55 g |
| C$_{20}$ hydrocarbon (internal standard) | 1.70 g |
| ethyl titanate | 0.09 g (0.39 mmole) |
| cuprous chloride | 0.10 g (1.01 mmole) |

After heating at 125° C. for 1 hour 30 minutes, the degree of conversion of dehydrolinalol is 98%. A mixture of neral and geranial (ratio: 0.65), with a yield of 65% relative to the dehydrolinalol converted, is thereby obtained.

EXAMPLE 28

The following are introduced, under an inert atmosphere, into a 25-cc three-necked round-bottomed flask equipped with a condenser, an inlet for argon, a partition-wall for sampling and a magnetic stirrer:

| 4-methylbenzoic acid | 2.4 g (17.63 mmoles) |
| dichlorobenzene | 13.1 g |
| bicyclohexyl (internal standard) | 3.46 g |

The following is added to the heterogeneous mixture at 20° C.:

titanium tetrachloride: 0.28 g (1.46 mmole)

The temperature rises to 25° C. and the reaction mixture becomes bright yellow coloured. The mixture is gradually heated to 100° C. and maintained at this temperature for 30 minutes, under a slight current of argon in order to remove the hydrochloride acid formed. The reaction mixture, which is chestnut-orange coloured, is homogeneous. After cooling to 40° C., the following are introduced:

| methylbutynol | 8.68 g (103.2 mmoles) |
| cuprous chloride | 0.2 g (2.02 mmoles) |

After heating at 130° C. for 30 minutes, the degree of conversion of methylbutynol is 99% and the yield of prenal is 80% relative to the methylbutynol converted.

EXAMPLE 29

The reaction is carried out as in Example 2, but using:

| methylbutynol | 8.68 g (103.2 mmoles) |
| 4-methylbenzoic acid | 2.4 g (17.6 mmoles) |
| dichlorobenzene | 13.1 g |
| bicyclohexyl (internal standard) | 3.46 g |
| titanyl acetylacetonate | 0.4 g (1.53 mmole) |
| cuprous chloride | 0.2 g (2.02 mmoles) |

After heating at 130° C. for 1 hour 30 minutes, the degree of conversion of methylbutynol is 99% and the yield of prenal is 85% relative to the methylbutynol converted.

EXAMPLE 30

The reaction is carried out as in Example 2, but using:

| methylbutynol | 8.68 g (103.2 mmoles) |
| dichlorobenzene | 13.1 g |
| bicyclohexyl (internal standard) | 3.46 g |
| 4-methylbenzoic acid | 2.4 g (17.6 mmoles) |
| titanocene dichloride | 0.38 g (1.53 mmole) |
| cuprous chloride | 0.2 g (2.02 mmoles) |

After heating at 130° C. for 2 hours, the degree of conversion of methylbutynol is 99% and the yield of prenal is 82% relative to the methylbutynol converted.

EXAMPLE 31

The following are introduced, under an argon atmosphere, into a 100-cc round-bottomed flask:

| 4-methylbenzoic acid | 2.4 g (17.6 mmoles) |
| acetic acid | 5.25 g |

| | |
|---|---|
| dichloroethane | 50 cc |
| titanium trichloride [in a 15% (w/v) aqueous solution] | 2.76 g (2.24 mmoles of TiCl$_3$) |

The mixture is heated to 85° C. and the dichloroethane-water azeotropic mixture is distilled. The reaction mixture which is initially purple and heterogeneous changes to dark violet and becomes homogeneous.

The following are then added:

| | |
|---|---|
| dichlorobenzene | 10 cc |
| anhydrous cupric chloride | 0.3 g (2.23 mmoles) |

The mixture is heated to reflux, removing the residual dichlorethane by distillation. The temperature of the reaction mixture reaches 120° C. The reaction mixture gradually becomes colourless, passing from dark violet to brown, to green, to yellow and then to white. A precipitate formation is observed. The following are added after cooling:

| | |
|---|---|
| bicyclohexyl (internal standard) | 3.46 g |
| methylbutynol | 8.68 g (103.2 mmoles) |

The mixture is heated. The white precipitate dissolves. The reflux temperature stabilizes at 115° C. and the pale yellow reaction mixture become homogeneous. The temperature is then increased rapidly to 130° C. and the mixture is heated at this temperature for 1 hour 30 minutes.

The degree of conversion of methylbutynol is 98% and the yield of prenal is 84% relative to the methylbutynol converted.

EXAMPLE 32

The reaction is carried out as in Example 2, but using:

| | |
|---|---|
| methylbutynol | 4.34 g (51.6 mmoles) |
| benzonitrile | 5.0 g |
| bicyclohexyl (internal standard) | 1.73 g |
| 4-methylbenzoic acid | 1.2 g (8.81 mmoles) |
| butyl titanate | 0.25 g (0.73 mmole) |
| cuprous chloride | 0.073 g (0.74 mmole) |

After heating at 130° C. for 1 hour 30 minutes, the degree of conversion of methylbutynol is 98% and the yield of prenal is 81% relative to the methylbutynol converted.

EXAMPLE 33

The reaction is carried out as in Example 2, but using:

| | |
|---|---|
| methylbutynol | 8.68 g (103 mmoles) |
| dichlorobenzene | 10 cc |
| bicyclohexyl (internal standard) | 4 cc |
| 4-methoxybenzoic acid | 2.7 g (17.76 mmoles) |
| butyl titanate | 0.56 g (1.67 mmoles) |
| cuprous chloride | 0.2 g (2.02 mmoles) |

After heating at 130° C. for 50 minutes, the degree pf conversion of methylbutynol is 96.4% and the yield of prenal is 85.8% relative to the methylbutynol converted.

EXAMPLE 34

The reaction is carried out as in Example 2, but using:

| | |
|---|---|
| methylbutynol | 8.68 g (103 mmoles) |
| dichlorobenzene | 10 cc |
| bicyclohexyl (internal standard) | 4 cc |
| 4-phenoxybenzoic acid | 3.8 g (17.76 mmoles) |
| butyl titanate | 0.56 g (1.67 mmole) |
| cuprous chloride | 0.2 g (2.02 mmoles) |

After heating at 130° C. for 1 hour 30 minutes, the degree of conversion of methylbutynol is 93.8% and the yield of prenal is 82.3% relative to the methylbutynol converted.

EXAMPLE 35

The reaction is carried out as in Example 2, but using:

| | |
|---|---|
| methylbutynol | 0.1 mole |
| dichlorobenzene | 25.4 g |
| octanoic acid | 0.0037 mole |
| butyl titanate | 0.00073 mole |
| cuprous chloride | 0.00081 mole |

After heating at 130° C. for 3 hours, the degree of conversion of methylbutynol is 97% and the yield of prenal is 80% relative to the methylbutynol converted.

EXAMPLE 36

The reaction is carried out as in Example 2, but using:

| | |
|---|---|
| methylbutynol | 0.1 mole |
| dichlorobenzene | 25.4 g |
| phenylacetic acid | 0.0037 mole |
| butyl titanate | 0.00073 mole |
| cuprous chloride | 0.00081 mole |

After heating at 130° C. for 3 hours, the degree of conversion of methylbutynol is 85% and the yield of prenal is 82% relative to the methylbutynol converted.

EXAMPLE 37

The reaction is carried out as in Example 2, but using:

| | |
|---|---|
| methylbutynol | 0.1 mole |
| dichlorobenzene | 25.4 g |
| 2-ethylhexanoic acid | 0.0074 mole |
| butyl titanate | 0.00073 mole |
| cuprous chloride | 0.00081 mole |

After heating at 130° C. for 3 hours, the degree of conversion of methylbutynol is 95% and the yield of prenal is 79% relative to the methylbutynol converted.

EXAMPLE 38

The reaction is carried out as in Example 2, but using:

| methylbutynol | 0.1 mole |
|---|---|
| dichlorobenzene | 25.4 g |
| heptanoic acid | 0.0074 mole |
| butyl titanate | 0.00073 mole |
| cuprous chloride | 0.00081 mole |

After heating at 130° C. for 2 hours 30 minutes, the degree of conversion of methylbutynol is 96% and the yield of prenal is 85% relative to the methylbutynol converted.

EXAMPLE 39

The reaction is carried out as in Example 2, but using:

| methylbutynol | 8.4 g (99.86 mmoles) |
|---|---|
| methyl benzoate | 17.9 g |
| bicyclohexyl (internal standard) | 4 g |
| heptanoic acid | 0.96 g (7.37 mmoles) |
| isopropyl titanate | 0.21 g (0.75 mmole) |
| cuprous chloride | 0.08 g (0.81 mmole) |

After heating at 130° C. for 3 hours, the degree of conversion of methylbutynol is 94% and the yield of prenal is 86% relative to the methylbutynol converted.

EXAMPLE 40

The reaction is carried out as in Example 2, but using:

| methylbutynol | 8.4 g (99.86 mmole) |
|---|---|
| anisole | 15 g |
| bicyclohexyl (internal standard) | 4 g |
| heptanoic acid | 0.96 g (7.37 mmoles) |
| isopropyl titanate | 0.21 g (0.75 mmole) |
| cuprous chloride | 0.08 g (0.81 mmole) |

After heating at 130° C. for 3 hours, the degree of conversion of methylbutynol is 97% and the yield of prenal is 87% relative to the methylbutynol converted.

EXAMPLE 41

The reaction is carried out as in Example 2, but using:

| methylbutynol | 8.4 g (99.86 mmoles) |
|---|---|
| phenetole | 15 g |
| bicyclohexyl (internal standard) | 4 g |
| heptanoic acid | 0.96 g (7.37 mmoles) |
| isopropyl titanate | 0.21 g (0.75 mmole) |
| cuprous chloride | 0.08 g (0.81 mmole) |

After heating at 130° C. for 3 hours, the degree of conversion of methylbutynol is 96% and the yield of prenal is 87% relative to the methylbutynol converted.

EXAMPLE 42

The reaction is carried out as in Example 2, but using:

| methylbutynol | 8.4 g (99.86 mmoles) |
|---|---|
| bicyclohexyl (solvent) | 12.4 g |
| tetradecane (internal standard) | 4 g |
| heptanoic acid | 0.96 g (7.37 mmoles) |
| isopropyl titanate | 0.21 g (0.75 mmole) |
| cuprous chloride | 0.08 g (0.81 mmole) |

After heating at 130° C. for 4 hours 45 minutes, the degree of conversion of methylbutynol is 77% and the yield of prenal is 95% relative to the methylbutynol converted.

EXAMPLE 43

A mixture (21 cc) consisting of the following is introduced into 34-cc glass tubes (Carius tubes):

| methylbutynol | 5.6 g (66.6 mmoles) |
|---|---|
| dichlorobenzene | 14.25 g |
| bicyclohexyl (internal standard) | 2.66 g |
| 4-methylbenzoic acid | 2.45 mmoles |
| isopropyl titanate | 0.49 mmole |
| cuprous chloride | 0.54 mmole |

The tubes are sealed under an inert atmosphere and then heated in an oven at 130° C.

After heating for 2 hours 30 minutes, the degree of conversion of methylbutynol is 98% and the yield of prenal is 90% relative to the ethylbutynol converted.

EXAMPLE 44

The reaction is carried out as in Example 2, but using:

| methylbutynol | 8.68 g (103.2 mmoles) |
|---|---|
| dichlorobenzene | 13.1 g |
| bicyclohexyl (internal standard) | 3.46 g |
| 4-methylbenzoic acid | 2.4 g (17.63 mmoles) |
| butyl titanate | 0.5 g (1.47 mmole) |
| cuprous chloride | 0.15 g (1.52 mmole) |

After heating at 130° C. for 1 hour, the degree of conversion of methylbutynol is 97% and the yield of prenal is 85% relative to the methylbutynol converted.

EXAMPLE 45

The reaction is carried out as in Example 2, but using:

| methylbutynol | 8.68 g (103.2 mmoles) |
|---|---|
| dichlorobenzene | 26.2 g |
| bicyclohexyl (internal standard) | 3.46 g |
| 4-methylbenzoic acid | 0.6 g (4.41 mmoles) |
| butyl titanate | 0.25 g (0.73 mmole) |
| cuprous chloride | 0.08 g (0.81 mmole) |

After heating at 130° C. for 2 hours 30 minutes, the degree of conversion of methylbutynol is 98% and the yield of prenal is 89% relative to the methylbutynol converted.

EXAMPLE 46

The reaction is carried out as in Example 2, but using:

| | |
|---|---|
| methylbutynol | 4.4 g (52.31 mmoles) |
| dichlorobenzene | 6.5 g |
| bicyclohexyl (internal standard) | 1.72 g |
| 4-methylbenzoic acid | 1.2 g (8.81 mmoles) |
| butyl titanate | 0.25 g (0.73 mmole) |
| copper oxalate, hemihydrate | 0.12 g (0.75 mmole) |

After heating at 130° C. for 5 hours, the degree of conversion of methylbutynol is 91% and the yield of prenal is 85% relative to the methylbutynol converted.

The copper oxalate is prepared in an aqueous medium by adding basic copper carbonate to oxalic acid. The blue precipitate formed is separated by filtration.

EXAMPLE 47

The following are introduced, under an inert atmosphere, into a round-bottomed flask equipped with a reflux condenser:

| | |
|---|---|
| dichlorobenzene | 19.5 g |
| 4-methylbenzoic acid | 1.8 g (13.2 mmoles) |
| butyl titanate | 0.37 g (1.09 mmole) |

The mixture is heated at 130° C. for 15 minutes. The butanol released condenses in the condenser. The butanol is distilled under reduced pressure (T=32° C.; p=13 mm Hg, 1.43 kPa) by heating the flask to 64° C. A mixture of butanol (90% of the theoretical quantity) and dichlorobenzene (2 cc) is thereby collected.

The following are then introduced into the flask

| | |
|---|---|
| dichlorobenzene | 2 cc |
| methylbutynol | 12.8 g (152.2 mmoles) |
| bicyclohexyl (internal standard) | 5.3 g |
| cuprous chloride | 0.11 g (1.11 mmole) |

After heating at 130° C. for 2 hours, the degree of conversion of methylbutynol is 97% and the yield of prenal is 88% relative to the methylbutynol converted.

EXAMPLE 48

The reaction is carried out as in Example 2, but using:

| | |
|---|---|
| methylbutynol | 8.4 g (99.86 mmoles) |
| methyl benzoate | 16.2 g |
| bicyclohexyl (internal standard) | 4 g |
| crotonic acid | 0.4 g (4.65 mmoles) |
| isopropyl titanate | 0.21 g (0.75 mmole) |
| cuprous chloride | 0.08 g (0.81 mmole) |

After heating at 130° C. for 1 hour, the degree of conversion of methylbutynol is 96% and the yield of prenal is 93% relative to the methylbutynol converted.

EXAMPLE 49

The reaction is carried out as in Example 2, but using:

| | |
|---|---|
| methylbutynol | 8.4 g (99.86 mmoles) |
| nitrobenzene | 17.8 g |
| bicyclohexyl (internal standard) | 4 g |
| heptanoic acid | 0.96 g (7.37 mmoles) |
| isopropyl titanate | 0.21 g (0.75 mmole) |
| cuprous chloride | 0.08 g (0.81 mmole) |

After heating at 130° C. for 2 hours, the degree of conversion of methylbutynol is 94% and the yield of prenal is 86% relative to the methylbutynol converted.

EXAMPLE 50

The reaction is carried out as in Example 2, but using:

| | |
|---|---|
| methylbutynol | 8.4 g (99.86 mmoles) |
| N—methylpyrrolidone | 15.3 g |
| bicyclohexyl (internal standard) | 4 g |
| heptanoic acid | 0.96 g (7.37 mmoles) |
| isopropyl titanate | 0.21 g (0.75 mmole) |
| cuprous chloride | 0.08 g (0.81 mmole) |

After heating at 130° C. for 2 hours, the degree of conversion of methylbutynol is 81% and the yield of prenal is 65% relative to the methylbutynol converted.

EXAMPLE 51

The reaction is carried out as in Example 2, but using:

| | |
|---|---|
| methylbutynol | 8.4 g (99.86 mmoles) |
| cyclohexanone | 14 g |
| bicyclohexyl (internal standard) | 4 g |
| heptanoic acid | 0.96 g (7.37 mmoles) |
| isopropyl titanate | 0.21 g (0.75 mmole) |
| cuprous chloride | 0.08 g (0.81 mmole) |

After heating at 130° C. for 2 hours, the degree of conversion of methylbutynol is 51% and the yield of prenal is 63% relaive to the methylbutynol converted.

EXAMPLE 52

The reaction is carried out as in Example 2, but using:

| | |
|---|---|
| 95% 3,7-dimethyl-3-hydroxy-7-methoxy-1-octyne (methoxydehydrolinalol) | 9.7 g (50 mmoles) |
| methyl benzoate | 7.0 g |
| dichlorobenzene (internal standard) | 4.5 g |
| crotonic acid | 0.2 g (2.323 mmoles) |
| butyl titanate | 0.13 g (0.382 mmole) |
| ouprous chloride | 0.04 g (0.404 mmoles) |

After heating at 130° C. for 2 hours, the degree of conversion of methoxydehydrolinalol is 98% and the yield of 3,7-dimethyl-7-methoxy-2-octenal is 72% relative to the methoxydehydrolinalol converted.

EXAMPLE 53

The reaction is carried out as in Example 2, but using:

| | |
|---|---|
| 91% 1-phenoxy-4-hydroxy-4-methyl-2-pentyne | 1.0 g (4.78 mmoles) |
| methyl benzoate | 10 g |

| | |
|---|---|
| crotonic acid | 0.1 g (1.16 mmole) |
| butyl titanate | 0.08 g (0.235 mmole) |
| cuprous chloride | 0.05 g (0.505 mmole) |

After heating at 170° C. for 4 hours, the degree of conversion of the acetylenic alcohol is 75% and the yield of 1-phenoxy-2-oxo-4-methyl-3-pentene is 63% relative to the acetylenic alcohol converted.

EXAMPLE 54

The following are introduced, under an argon atmosphere, into a round-bottomed flask surmounted by a Virgreux column followed by a condenser and a receiver:

| | |
|---|---|
| 2-butyn-1-ol | 1.9 g (26.57 mmoles) |
| dichlorobenzene | 14 g |
| bicyclohexyl (internal standard) | 2 g |
| crotonic acid | 0.28 g (3.25 mmoles) |
| butyl titanate | 0.18 g (0.53 mmole) |
| cuprous chloride | 0.1 g (1.04 mmole) |

The mixture is heated at 130° C. for 30 minutes and then at 140° C. for 2 hours. The light products, entrained by an argon current, are collected in the receiver which is cooled externally with an acetone-solid carbon dioxide mixture. 1.46 g of distillate and thereby collected.

2-Butyn-1-ol and methyl vinyl ketone are determined in the distillate and in the distillation residue.

The degree of conversion of 2-butyn-1-ol is 70% and the yield of methyl vinyl ketone is 67% relative to the 2-butyn-1-ol converted.

The yield of methyl vinyl ketone isolated is 61%.

I claim:

1. A process for the preparation of the ethylenic carbonyl compound of formula:

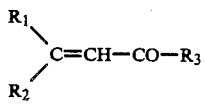

in which $R_1$, $R_2$ and $R_3$, which may be identical or different, each represent a hydrogen atom or a saturated or unsaturated aliphatic radical, or $R_1$ and $R_2$ together form a cycloaliphatic radical and $R_3$ represents a hydrogen atom or a saturated or unsaturated aliphatic radical, the aforesaid aliphatic radicals being unsubstituted or substituted by one or more substituents, which may be identical or different, chosen from alkoxy and phenoxy, which comprises causing the isomerization of an acetylenic alcohol of formula:

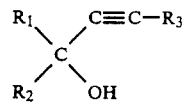

in which $R_1$, $R_2$ and $R_3$ are as defined above, by heating the said acetylenic alcohol in a liquid phase in the presence of a catalytic system which consists of (1) a titanium derivative which is a titanium chelate, titanium trichloride or tetrachloride, titanocene dichloride, or a compound of formula $Ti(R)_4$ in which each symbol R, which may be the same or different, is a radical $OR'$ or $OCOR'$ in which $R'$ is an alkyl radical of 1 to 4 carbon atoms; (2) a copper or silver derivative which is an inorganic or organic acid salt; and optionally (3) an inorganic or organic acid, which may be in the form of an ester or an anhydride, chosen from saturated or unsaturated aliphatic acids or diacids containing 1 to 20 carbon atoms and aromatic acids and diacids, which may be unsubstituted or substituted, or an inorganic phosphoric acid or sulphonic acid ester; and isolating the ethylenic carbonyl compound obtained.

2. Process according to claim 1, wherein the radicals $R_1$, $R_2$ and $R_3$ together contain 2 to 30 carbon atoms and at least one of the radicals $R_1$ and $R_2$ is a hydrogen atom or an unsubstituted or substituted saturated or unsaturated alkyl radical containing 1 to 15 carbon atoms.

3. Process according to claim 1, wherein the titanium derivative is a derivative of titanium with a degree of oxidation of II, III or IV.

4. Process according to claim 3, wherein the titanium derivative is an alkyl titanate, titanium dibutoxy-bis-acetylacetonate, titanium trichloride or tetrachloride, titanyl acetylacetonate, or titanocene dichloride.

5. Process according to claim 1, wherein the copper or silver derivative is cuprous chloride, cupric chloride, cupric oxalate or silver trifluoroacetate.

6. Process according to claim 1, wherein the catalytic system contains an inorganic or organic acid ester, an acid anhydride, or an organic acid.

7. Process according to claim 6, wherein the catalytic system comprises acetic, hexanoic, heptanoic, 2-ethylhexanoic, octanoic, adipic, crotonic, benzoic, 4-methylbenzoic, 4-methoxybenzoic, 4-phenoxybenzoic, phenylacetic or terephthalic acid.

8. Process according to claim 6, wherein the catalytic system comprises 0.01 to 1 mole of acid or derivative thereof per mole of acetylenic alcohol employed.

9. Process according to claim 1 wherein the catalytic system comprises 0.005 to 0.05 mole of titanium derivative and 0.005 to 0.1 mole of copper or silver derivative per mole of acetylenic alcohol employed.

10. The process according to claim 1, wherein the reaction is carried out at a temperature of 80° to 180° C.

11. Process according to claim 1, wherein the reaction is carried out in an organic solvent which is an aliphatic, alicyclic or aromatic hydrocarbon, which is unsubstituted or substituted by one or more substituents chosen from halogen, alkoxy, nitro and cyano, an amide or a ketone.

* * * * *